US010292997B2

(12) United States Patent
Lindenbaum (10) Patent No.: US 10,292,997 B2
(45) Date of Patent: May 21, 2019

(54) COMPOSITIONS AND METHODS FOR STIMULATING WOUND HEALING (75) Inventor: Ella Lindenbaum, Brentwood, CA (US)

(73) Assignee: Daniel N. Rastein, Calabasas, CA (US)

(*) Notice: Subject to any disclaimer, the term of this patent is extended or adjusted under 35 U.S.C. 154(b) by 91 days.

(21) Appl. No.: 13/066,340

(22) Filed: Apr. 12, 2011

(65) Prior Publication Data
US 2012/0183630 A1 Jul. 19, 2012

Related U.S. Application Data (60) Provisional application No. 61/433,378, filed on Jan. 17, 2011.

(51) Int. Cl.
| A61K 31/765 | (2006.01) |
| A61K 9/00 | (2006.01) |
| A61K 9/06 | (2006.01) |
| A61K 36/54 | (2006.01) |
| A61K 36/9066 | (2006.01) |
| A61K 38/28 | (2006.01) |
| A61K 38/30 | (2006.01) |
| A61K 45/06 | (2006.01) |
| A61K 47/36 | (2006.01) |

(52) U.S. Cl.
CPC .......... *A61K 31/765* (2013.01); *A61K 9/0014* (2013.01); *A61K 9/06* (2013.01); *A61K 36/54* (2013.01); *A61K 36/9066* (2013.01); *A61K 38/28* (2013.01); *A61K 38/30* (2013.01); *A61K 45/06* (2013.01); *A61K 47/36* (2013.01)

(58) Field of Classification Search
CPC . A61K 31/765; A61K 9/0014; A61K 36/9066
See application file for complete search history.

(56) References Cited

U.S. PATENT DOCUMENTS 5,591,709 A * 1/1997 Lindenbaum ........ A61K 31/545
424/484

FOREIGN PATENT DOCUMENTS

| CA | 2532352 A1 | 1/2005 |
| WO | 0243751 A1 | 6/2002 |

OTHER PUBLICATIONS

Science Daily, Why Applying Insulin to Wounds Significantly Enhances Healing, American Society of Cell Biology, 2006 (Year: 2006).*
Kannappan (Cinnamon bark extract improves glucose metabolism and lipid profile in the fructose-fed rat, Singapore Med J 2006; 47 : 858) (Year: 2006).*
Kannappan (Cinnamon bark extract improves glucose metabolism and lipid profile in the fructose-fed rat, Singapore Med J 2006; 47 : 858, of record) (Year: 2006).*
Katakam, et al. (Cerebrovascular responses to insulin in rats, J Cereb Blood Flow Metab. 2009, 29: 1955) (Year: 2009).*
Moriyama, et al. (Regulated insulin release from biodegradable dextran hydrogels containing poly(ethylene glycol), Journal of Controlled Release 1996, 42: 237-248). (Year: 1996).*
Anderson (Chromium and insulin resistance, Nutrition Research Reviews 2003, 16: 267-275) (Year: 2003).*
Katakam (Cerebrovascular responses to insulin in rats, J Cereb Blood Flow Metab. 2009, 29:1955) (Year: 2009).*
Anderson RA, et al. Isolation and Characterization of Polyphenol Type-A Polymers from Cinnamon with Insulin-like Biological Activity. J. Agric. Food Chem., 2004, 52(1):65-70. (Abstract only).
Berrio LF, et al. Insulin Activity: Stimulatory Effects of Cinnamon and Brewer's Yeast as Influenced by Albumin. Horm Res, 1992, 37:225-229. (Abstract only).
Jarvill-Taylor KJ, et al. A Hydroxychalcone Derived from Cinnamon Functions as a Mimetic for Insulin in 3T3-L1 Adipocytes. Journal of the American College of Nutrition, 2001, 20(4):327-336.
Kamath JV, et al. Pro-healing Effect of Cinnamomum zeylanicum Bark. Phytotherapy Research, 2003, 17:970-972.
Lindenbaum E, et al., Serum-free cell culture medium induces acceleration of wound healing in guinea-pigs. Burns, 1995, 21:110-115.
Lindenbaum E, et al. Preliminary clinical trials of serum free cell culture medium as a treatment for chronic atrophic ulcers. Eur J Plast Surg, 1997, 20:115-121.
Lindenbaum E, et al. Stimulated Healing of Recalcitrant Wounds by Topical Application of Enriched Cell Culture Medium: A Clinical Report. Plastic and Reconstructive Surgery, 2001, 108(1):104-113.
Mulder GD, If Wounds Could Talk, Clinical and Experimental Approaches to Dermal and Epidermal Repair; Normal and Clinical Wounds, Wiley-Liss, Inc, 1991, pp. 55-66.
Nakao H, et al., Mixture of sugar and povidone-iodine stimulates wound healing by activation keratinocytes and fibroblast functions. Arch Dermatol Res, 2006, 298:175-182.
Schilling JA, et al. Fractional Analysis of Experimental Wound Fluid. Proc Soc Exp Biol Med, 1955, 89:189-192.
Stapleton SR, Selenium: an insulin-mimetic. Cell. Mol. Life Sci., 2000, 57:1874-1879.

(Continued)

Primary Examiner — Karlheinz R. Skowronek
Assistant Examiner — Khalid Kader
(74) Attorney, Agent, or Firm — Daniel L. Dawes; Marcus C. Dawes (57) ABSTRACT The present invention relates to compositions and methods to improve the microenvironments in and around the wound in an effort to enhance healing. Specifically, the present invention comprises application of tissue and cells culture nutrient media, such as minimum essential media, supplemented with insulin and/or with substances exhibiting insulin-like activity, such as cinnamon or cinnamon extracts including but not limited to MHCP. The media is applied to the wound to stimulate the viable cells in the wound bed and the adjacent cells in the periphery of the wound to proliferate and grow into the wound in order to achieve wound closure.

4 Claims, 3 Drawing Sheets (56) References Cited

OTHER PUBLICATIONS

White BN, et al. Wound Healing: Investigation of Proteins, Glycoproteins, and Lipids of Experimental Wound Fluid in the Dog. Proc Soc Exp Biol Med, 1958, 101:353-360.

* cited by examiner

COMPOSITIONS AND METHODS FOR STIMULATING WOUND HEALING

RELATED APPLICATIONS

The present application claims the benefit of priority of provisional application Ser. No. 61/433,378, filed Jan. 17, 2011, entitled "Compositions and Method for Stimulating Wound Healing", the entire contents of which application is incorporated by reference herein.

FIELD OF THE INVENTION

The purpose of this invention is to improve the microenvironments in and around the wound. Specifically, it comprises of application of tissue and cells culture nutrient media, such as minimum essential media, supplemented with insulin and/or with substances exhibiting insulin-like activity, such as cinnamon or its extract methyl hydroxyl chalcone polymer (MHCP). The media is applied to the wound to stimulate the viable cells in the wound bed and the adjacent cells in the periphery of the wound to proliferate and grow into the wound in order to achieve wound closure. Compositions according to the present invention, especially compositions which include MHCP or preferably both MHCP and insulin in effective amounts exhibit synergistic activity in stimulating wound healing, especially including non-healing, chronic wounds, in patients.

BACKGROUND OF THE INVENTION

A wound is defined as a break in the continuity of the skin. It can be caused by traumatic injury such as burn, cut or scrape. A prompt treatment will avoid complications such as infection and inflammation. The usual and conservative methods of closing a wound are application of various medicaments or alternatively, the wound is closed by surgical procedures of suturing the wounds edges, by grafting cultured skin or by split skin grafts. The aim of all of the above is to promote the growth of granulation tissue that may or may not follow promptly, depending on adequate blood supply bringing into the wound the nutrients that the cells need for growth.

The concept of this method is to use a proactive rather then protective treatment. That is, following the usage of antiseptic or anti-inflammatory medicaments, that when indicated are the standard treatments, the treatment then should be followed by induction of a stimulatory treatment.

The idea is to create microenvironment favorable for wound healing after assuring that the wound is clinically clean. This method aims to stimulate and support growth of connective tissue components originating from the wound bed and its peripheral walls. The granulation tissue filling the wound space will create the substratum required for re-epithelialization and wound closure.

When injury to the skin occurs, a set of complex biochemical events takes place in a cascade leading to repair the damage.

Wound healing, or wound repair, is an intricate process in which the skin (or another organ-tissue) repairs itself after injury. In normal skin, the epidermis (outermost layer) and dermis (inner or deeper layer) exists in steady-state equilibrium, forming a protective barrier against the external environment. Once the protective barrier is broken, the normal (physiologic) process of wound healing is immediately set in motion.

The classic model of wound healing is divided into three or four sequential, yet overlapping, phases: (1) homeostatic, (2) inflammatory, (3) proliferative and (4) remodeling.

1. Homeostasis occurs shortly after the injury; platelets (thrombocytes) migrate to the injury site to form a fibrin clot. This clot acts to control active bleeding.

2. During the inflammatory phase, bacteria and debris are removed by phagocytosis and the simultaneous release of growth factors causes migration and division of the cells that take part in the proliferative phase.

3. The proliferative phase of wound healing is characterized by angiogenesis, collagen formation and deposition, growth of granulation tissue, epithelialization, and wound contraction. Angiogenesis involves formation of new blood vessels by the vascular endothelial cells. During the fibroplasia and the granulation tissue formation, the fibroblasts grow and form a new, provisional extra cellular matrix by excreting collagen and fibronectin. Concurrently, re-epithelialization of the epidermis occurs, where epithelial cells proliferate and migrate over the granulation tissue, providing cover for the new tissue.

4. Remodeling phase comprises the contraction process where the wound becomes smaller due to contraction of myofibroblasts that grip the wound edges and contract. In the maturation and remodeling phase, collagen is remodeled and realigned along tension lines and cells that are no longer needed are removed by apoptosis.

However, the healing is process that is not only complex but also fragile, and susceptible to interruption or failure leading to the formation of chronic non-healing wounds. Factors which may contribute to this include diabetes, topical or systemic venous and/or arterial insufficiencies, old age, and infection.

Thus, a wound is defined as a break in the continuity of the skin. It can be caused by traumatic injury such as burn, cut or scrape. A prompt treatment will avoid complications such as infection and inflammation. The usual and conservative methods of closing a wound are application of various medicaments or alternatively, the wound is closed by surgical procedures of suturing the wounds edges, by grafting cultured skin or by split skin grafts. The aim of all of the above is to promote the growth of granulation tissue that may or may not follow promptly, depending primarily on adequate blood supply that brings into the wound the nutrients that the cells need for growth.

The concept of this method is to use a proactive rather then protective treatment. That is, following the usage of antiseptic or anti-inflammatory medicaments, that when indicated are the standard treatments, the treatment then should be followed by induction of a stimulatory treatment.

The idea is to create a microenvironment favorable for wound healing after assuring that the wound is clinically clean. The wound and its surrounding area will be moisturized, exposed to the rich nutrients, protected from dehydration by the gelling of the media and dressed with sterile gauze which allows the oxygen in the air to penetrate the dressing and reach the wound surface. This method aims to stimulate and support growth of connective tissue components originating from the wound bed and its peripheral walls. The proliferating granulation tissue filling the wound space will create the substratum required for re-epithelialization leading to wound closure.

This invention is based on human tissue and cell culture technology of growing fibroblast and epithelial cells in culture. Utilizing similar nutrient media supplements with insulin or alternatively with substances possessing insulin-mimetic features, the milieu in the wound becomes moist and enriched with the nutrients. These are the requirements for cells proliferation and the growth of the granulation tissue including new capillaries into the wound space.

Wound healing involving surgical procedures are successful only when the application of the graft is performed onto viable granulation tissue. Success of the graft take is dependent on the proliferation of granulation tissue that can be achieved only when adequate microenvironment is created in the wound. Thus the viability of the grafted tissue over the wound is the limiting by the availability of the materials for obtaining success of the take and the healing process.

There are multiple causes of injuries, damage by exposure to excessive hot or cold temperatures, mechanical damage by scraps, stabs or cuts, chemical damage due acid or alkaline burns or damage by radiation. All of these wounds heal by proliferation of granulation tissue that fills the space within the wound and is followed by growth of epithelial cells that invade the wound space from the bed and the periphery of the wound forming the new granulation tissue and culminating in complete wound closure. However, if the wound is infected or if the blood supply is insufficient for tissue growth, the healing process fails. In the first case application of antiseptics can overcome the contamination and eventually the wound will close, but in the second case of insufficient blood supply the wound becomes chronic. Serum-free cell culture media supplemented with insulin or substances with insulin-like activity (e.g. MHCP or MHCP and insulin-like growth factor, preferably human), preferably a mixture of insulin and a substance with insulin-like activity will supply the cells in the wound with the nutrients required for the process of wound healing.

From antiquity till today the beneficial effects of cinnamon were recognized. It was used as an ingredient of the sacred oil (Exodus 30:23) and as a spice (Proverbs 7:17, Song of Solomon 4:14 and Revelation 18:13). Furthermore, the essential oil of cinnamon extracted from the cinnamon bark was traditionally used as anti bacterial, anti microbial, anti infectious, anti viral and anti fungal agent. It was also used to increase blood flow in areas where the circulation was restricted. Majno G. in his book The Healing Hand, describes ancient methods of treating wounds including the used of honey as a powerful bacteriostatic agent and the use of cinnamon for its beneficial properties on wound healing.

Berrio L. F et al., report that cinnamon and Brewer's yeast potentates the activity of insulin. In two publications, in Jarvill-Taylor J. Anderson R. A. et. al., and in Karlee J. Jarville-Taylor et. al. demonstrated the insulin-like activity was found in substances including cinnamon. They report that, in adipocytes cell cultures, Methyl Hydroxy Chalcone Polymer-(MHCP), extracted from cinnamon, acts as a mimetic of insulin. This component that is found in cinnamon affects glucose metabolism and the conversion of glucose to energy that then is utilized to enhance the cells multiplication process. In addition it renders insulin much more efficient and thus acts synergistically with insulin. In addition, Kamath J. V et. al., report the hydroxyproline increase in the granulation tissue content of the wound due to treatment with cinnamum zeylanicum. Anderson R, et. al recently describes the effectiveness of polyphenol type-A polymer extracted from cinnamon as a powerful insulin mimetic substance.

Karalee J. T. and Stapleton S. R. reported the usage of cinnamon extract to boost insulin sensitivity and that Selenium was implicated in potentiating the insulin-like activity since it stimulates glucose uptake and regulates glycolysis, gluconeogenesis and fatty acids synthesis. Alt S. et al., describes using insulin and other agents to work in synergy to accelerate the healing process. However neither of them used serum-free cell culture media such as MEM, DMEM, BGJ or MCDB as a substrate.

Insulin has been implicates in triggering the cascade of the wound healing process. C. Linge claims that when insulin is injected into the wound area it enhances re-epithelialization of the wound. It is well known that sugar has been successfully used in treating wounds during the First World War, and honey has been used since antiquity to treat wounds both with definite success. Nakao H. et. al. reports that the mixture of sugar and povidone-iodine stimulated wound healing by stimulating the keratinocytes and fibroblasts activity.

In a series of clinical trials Lindenbaum E. S. et al., used a formulation containing serum-free cell culture nutrient medium MCDB 153 to successfully treat atrophic recalcitrant wounds. Lindenbaum E. S et al. also reported the successful use of serum-free cell culture media MCDB 153 supplemented with insulin to treat recalcitrant chronic wounds.

OBJECTS OF THE PRESENT INVENTION

It is the object of the present invention to describe a new method for stimulating wound-healings by treating wounds including, but not limited to, chronic recalcitrant wounds.

Another object of this invention is to provide compositions and methods to enhance the healing of wounds and of the adjacent tissues surrounding the wound.

Another object is to treat the wounds by using a combination of readily available and recognizable constituents.

Another object is to create and support an optimal microenvironment in and around the wound thus creating a favorable optimal moisturized nutrient rich milieu for the process of wound healing.

Another object to a polymer delivery system is to provide compositions and methods that stimulate the cells in the wound by creating moist environment using a gelled delivery system.

Any one or more of these and/or other objects of the invention may be readily gleaned from the detailed description of the invention which follows.

BRIEF DESCRIPTION OF THE INVENTION

This invention is based on human cell culture technology that grows fibroblast and epithelial cells in culture. By using similar nutrient media supplemented by insulin and/or by substances possessing insulin-like activity, the milieu in the wound becomes moist and enriched with nutrients capable of supplying all the requirements the cells need to proliferate and grow into the wound space. Preferred aspects of the invention comprise treating wounds in a cellular nutrient medium in combination with a substance possessing insulin-like activity and/or insulin. It has unexpectedly been discovered that the treatment of wounds may be synergistically enhanced by exposing wounds in a patient to a composition comprising an effective amount of MHCP or polyphenol type-A polymer and/or a non-steroidal anabolic hormone in a cellular nutrient medium, optionally and preferably in combination with an effective amount of insulin.

The formulation of this invention fulfills the requirements needed for promoting wound healing. The formulation contains effective amounts of cellular nutrient medium such as minimum essential medium MEM or serum-free cell culture media as otherwise disclosed herein, for example, MEM, DMEM, BGJ or MCDB 153. The said media is supplemented with an effective amount of insulin, a non-steroidal anabolic hormone such as insulin-like growth factor (preferably human), or alternatively by insulin-like substances such as cinnamon or its extracts (e.g. MHCP, or polyphenol type-A polymer), chromium, curcuma or selenium.

The preferred embodiment according to the present invention is the non-steroidal anabolic hormone is insulin. In further preferred embodiments, the formulation also includes agents that mimic the insulin physiological activity such as cinnamon or its extracts that promote the entry of glucose into cells and converting it to energy. This energy can be utilized for regeneration of granulation tissues.

In general, insulin is included in compositions according to the present invention at concentrations ranging from about 5 ng/ml (nanograms per milliliter) to about 100 ug/ml (microgram per milliliter) [corresponding to about 120 uUnits/m (micro Units per milliliter) to about $24 \times 10^5$ uUnits/ml—approximately 0.0000005% to about 0.01% by weight], preferably about 500 ng/ml to about 500 ng/ml to about 50-10 ug/ml (about $1.2 \times 10^4$ uUnits/ml to about $1.2 \times 10^5$ uUnits/ml—about 0.00005% to about 0.0005% by weight of the treatment composition based upon the assumption that 1 ml of solution is equal to about t gram in weight). It is noticed that the amount of insulin of the instant invention maybe modified according to the length of storage time prior to use. In compositions that are applied in solid or concentrated form, i.e. as a gel, crème, lotion, elixir, powder or the like the anabolic hormone is included in concentrations similar to those contained in the solutions, and preferably comprises about 0.00000005% to about 0.000005% by weight of the wound treatment composition (based upon the general assumption that 1 ml of solution is approximately equal to about 1 gram in weight of the final composition). Percent weights may fall outside of these ranges, depending upon the wound treated, the level of stability of the hormone and other factors, as well recognized by one of ordinary skill in the art.

Among the world most frequently consumed spices cinnamon is water-soluble and is relatively inexpensive. Cinnamon may be a substituted for insulin since it is a substance that mimic insulin physiological activity. According to Anderson et. al., it's most active derivative methyl hydroxy chalcone polymer (MHCP) function as insulin in 3T3-L adipocytes cell cultures and was most effective in increasing glucose metabolism. Other substances such as the cinnamon derivatives MHCP or polyphenol type-A polymer, selenium, chromium, curcuma and insulin-like growth factor (especially human IGF) also known to mimic insulin activity may also be used as a substitute. The biological activity of MHCP at concentrations of about 0.1 mg/ml is about equivalent to the range of activity of 100 nM of insulin. Preferred MHCP concentration within the preferred media MCDB 153 ranges from about 0.01 mg/ml to about 1 mg/ml. Preferably the MHCP in media ranges from about 0.025 mg/ml to about 0.5 mg/ml. In preferred aspects of the invention, MHCP and insulin are combined in cellular nutrient medium to provide compositions according to the present invention. In addition, insulin-like growth factor (IGF) may also be added to the present invention in effective amounts to promote wound healing, especially in chronic wounds. The inclusion of selenium, chromium and/or curcuma as optional insulin-like agents assists in promoting wound healing of chronic wounds according to the present invention.

DETAILED DESCRIPTION OF THE INVENTION

In describing the present invention in the specification, a number of terms are used. The term wound is used throughout the specification to describe skin wounds, which are treated, by the formulations and the method according to the present invention. A skin wound is defined herein as a breach in the continuity of the skin that is caused by direct injury to the skin. Skin wounds are generally characterized by several types: punctures, incisions, including those produced by a variety of surgical procedures, excisions, lacerations, atrophic skin or necrotic wounds and burns, including large burn areas. The formulation according to the present invention is used in varying degrees for enhancing the healing of all types of wounds of the skin, including those which occur after a mesh autograph procedure. Compositions according to the present invention are unexpectedly effective to treat chronic wound conditions.

The term "delivery polymer" is used throughout the specification to describe a polymer which can be used in combination with a cellular nutrient medium (preferably, serum free), a non-steroidal anabolic hormone insulin or insulin-like substances and mixtures thereof, and optionally, individually which are preferably used for topical application to the treated wounds according to the present invention. These delivery systems polymers include, for example, numerous hydrogels in hydrated or unhydrated form, such as those derived from hydroxyethylmetacrylate (HEMA), glycerolmetacrylate (GMA) and polyvinylpyrrolidone (PVP), polyethylene glycol (PEG) and various carbohydrates, cellulose, and related hydrophilic cellulose polymers, dextran, polyethyleneoxide, dextran-polyethylene, acrylamide, amylase, collagen, gelatin, sepharose, agarose (for example, as an agarose saturated gel), related polymers and mixtures thereof, among numerous others. One of ordinary skill in the art will recognize to vary the type and amount of delivery polymer in compositions according to the present invention to provide enhanced wound healing characteristic appropriate for topical delivery. The term delivery polymer is also used to describe polymers that provide slow-release or sustained release characteristics to the wound healing formulations of the invention. The term "gelling agent" is used to describe those polymers, which may be included in aqueous formulations according to the present invention in effective amounts to gel these formulations.

The term "methyl hydroxy chalcone polymer" (MHCP) is used to describe a component of cinnamon which functions similar to insulin in 3T3-L adipocytes cell cultures and were most effective in increasing glucose metabolism and may be used as a substitute for insulin or in addition to insulin pursuant to the present invention. Compositions which include effective amounts of MHCP and insulin and optionally, at least one further component selected from the group consisting of insulin-like growth factor (IFG), polyphenol type-A polymer, selenium, chromium, curcuma and mixtures thereof are preferred aspects of the invention because of the synergistic favorable impact such components have on wound healing, especially the healing of chronic wounds.

In general, MHCP is included in compositions according to the present invention in an effective amount, generally at concentration ranging from about 0.001 mg/ml to about 25 mg/ml, about 0.01 mg/ml to about 10 mg/ml, about 0.025 mg/ml to about 5 mg/ml, although concentrations outside of these ranges are also useful. In certain preferred aspects of the invention, the MHCP ranges from about 0.025 mg/ml to about 0.5-1.0 mg/ml. By way of a standard, in general, the biological of activity of 0.1 mg/ml of MHCP is approximately equivalent to the biological activity of about 100 nM of insulin. Percentage weights may fall outside of these ranges, depending upon the type and size of the wound and other factors, as well recognized by one of ordinary skill in the art.

Thus, the biological activity of MHCP at concentrations of about 0.1 mg/ml is about equivalent to the range of activity of 100 nM of insulin. Preferred MHCP concentration within the preferred media MCDB 153 ranges from about 0.01 mg/ml to about 1 mg/ml. Preferably the MHCP in MCDB 153 ranges from about 0.025 mg/ml to about 0.5 mg/ml.

According to Anderson et al. polyphenol type-A polymers found in cinnamon may function as antioxidants, and act as synergistic agents to insulin by potentiating its action and by also contributing to the control of glucose tolerance and diabetes.

The term "cellular nutrient medium" or "cellular nutrient mixture" is used throughout the specification to describe a medium or mixture (generally, at least a minimum essential medium) which preferably contains no serum (is serum-free), and in combination with insulin or insulin-like substances (e.g. MHCP, poly/phenolic type-A polymer, insulin-like growth factor, selenium, chromium, curcuma and mixtures thereof), at least one of them comprising the wound healing compositions according to the present invention. The nutrient medium, preferably serum-free, according to the present invention comprises the following elements: (a) essential amino acids; (b) non-essential amino acids; (c) vitamins selected from a group consisting of biotin, folate, lipoate, niacinamide, pantothenate, pyrodine, riboflavin, thiamin and vitamin $B_{12}$ and mixtures thereof, preferably a vitamin mixture comprising folate, niacinamide, pantothenate, pyrodine, riboflavin and thiamin; (d) glucose; and (e) a mixture of inorganic ions selected from a group consisting of calcium, sodium, potassium, magnesium, chloride and mixtures thereof, preferably a mixture comprising calcium, potassium, magnesium and chloride. All of these elements (a), (b), (c), (d) and (e) are included with the anabolic hormone and optionally the insulin like substances in concentrations and/or amounts effective for enhancing the growth of cells which surround, have been injured by or are responsible for healing a wound. The preferred concentration of essential and non-essential amino acids used in the present invention is from about 5.0 um ($10^{-6}$ mole) to about 50 mmol. ($10^{-3}$ mole). The proffered concentration of vitamins used in the present invention ranges from about 1 nanomole ($10^{-9}$ mol.) to about 10 um. The preferred concentration of glucose used in this invention ranges from about 1 umol. to about 10 or more mmol. In case of elements (e), these organic ions are preferably included in the present compositions are at concentration ranges of about 1 umol to about 50 mmol.

In addition to the elements (a), (b), (c), (d) and (e), the nutrient medium according to the present invention optionally contain any one of one or more of the following element: (f) purines and pyrimidines; (g) other organic compounds; (h) other inorganic ions; (i) trace elements; (j) buffers and indicators and (k) other supplements. All of the optional elements (f), (g), (h), (i), (j) and (k), when they are included in the nutrient medium according to the present invention are included in the amounts effective for enhancing the growth of cells involved in wound healing processes in combination with insulin or its mimicking substitute cinnamon or MHCP, further including an effective amount of insulin-like growth factor, IGF, selenium, chromium, curcuma and mixtures thereof. Preferably, components (f), (g), (j) and (k) range in concentration from about 1 mmol to about 10 mmol. In the case of components (h) and (j) the concentration preferably ranges from about 1 umol. to about 50 mmol. One of ordinary skill in the art will be able to readily modify the type and amount of the components of the cellular nutrient medium within the teaching of the present invention.

In addition to serum free cellular nutrient medium, the present invention may also make use of cellular nutrient medium containing serum, although the use of serum containing cellular nutrient medium is generally less preferred than is serum free medium. Examples of such nutrient medium include, among numerous others, DMEM, HAM F12 and HAM F10, all containing serum. The term "cellular nutrient medium" or "nutrient mixture" is used to describe all types of nutrient medium contemplated for the use in the present invention which contain at least the basic elements (generally, of a minimum essential medium) as described hereinabove, and such term includes serum free cellular nutrient medium.

The cellular nutrient medium according to the present invention includes one or more commercially available media in solution or lyophilate (solid) form. The cellular nutrient medium used may be in the form of a lyophilate which may be reconstructed with water, preferably sterilized, distilled water and then supplemented with the anabolic hormone insulin or cinnamon or hydroxychalcone or polyphenol type-A polymer or mixtures thereof, and optionally, by each one separately and further including optional components IGF, selenium, chromium or curcuma and mixtures thereof. Alternatively, the nutrient medium may be used directly in formulations according to the present invention in the form of a lyophilate, or related solid-type material, rather than a solution, especially when gels, creams, elixirs, powders or other delivery vehicles are to be used for delivery. It is clearly preferred when utilizing solid-type materials for delivering the wound healing compositions according to the present invention that the delivery system in the form of a hydrogel or other form containing moistening quantities of water.

Many of the commercially available media (preferably, serum free) are available from suppliers such as Collaborative Research Incorporated, Bedford, GIBCO, Grand Island, N.Y., or Biological Industries, Beth HaEmek, Israel. These media may be used as purchased or modified within the scope and practice of the present invention.

The term "non-steroidal anabolic hormone" is used throughout the specification to describe the primary hormone in the instant invention that promotes wound healing in combination with cellular nutrient media. The primary hormone is insulin or alternatively a nutrient substitute such as cinnamon, or other natural product which contains effective amounts of MHCP itself or polyphenol type-A polymer. As used herein, the term non-steroidal anabolic hormone includes naturally isolated (preferably human) or synthetically produced versions of insulin that are known to function substantially the same as the naturally occurring hormone and includes, where relevant, compounds produced by genetic engineering processes and techniques.

The non-steroidal anabolic hormone that is especially preferred is insulin. While not being limited by way of theory, it is believed that the inclusion of at least one selected from the two, insulin or MHCP and preferably both components, serves to enhance the effect of the nutrient media in increasing the rate and natural process of wound healing. Thus, it is believed that the non-steroidal anabolic hormone actually enables the wound cells to utilize or process the nutrient in the media, which action result in an enhanced rate of wound healing. A combination of insulin and MCHP in effective amounts as otherwise described herein is shown to be synergistic in enhancing wound healing.

The amount of each component, which is used in the formulation according to the present invention, will depend upon the type and size of the wound, but each component preferably is included in the amount effective for significantly enhancing the healing of a wound relative to traditionally wound healing therapies. In general, in embodiments according to the present invention, the formulation include an anabolic hormone or similar agent such as IGF and/or insulin in concentrations of at least about 0.005 ng/ml preferably about 0.5 ng/ml to about 50 ng/ml or more, more preferably about 50 ng/ml to about 20 ng/ml or more. In the case of formulations containing insulin, the amount of insulin generally falls outside of this range, because of its tendency to degrade and become inactive a more rapid rate then other anabolic hormones. Stabilized form of insulin could obviously be used at concentrations outside the above range. Preferably, the anabolic hormone is insulin and/or a cinnamon extract as insulin substitute such as methylhydroxychalcone polymer or polyphenol type-A polymer, further including one or more of selenium, insulin-like growth factor, chromium, curcuma and mixtures thereof and because of the benefit this hormone or its substitute(s) have in promoting the growth and elaboration of cells and their generally absence of toxicity. The preferred anabolic hormone is human insulin, which is well-known protein is readily commercially from a number of sources (for example, Sigma Chemical Co., USA or Novo Nordisk, Copenhagen, Denmark). It is constituted from a number of amino acids (approximately 51) with a total molecular weight of about 5,500. Human insulin for use in the present invention is generally prepared using genetic engineering techniques. Depending upon the manufacturer, the insulin may have slightly different activity based upon its weight; however the activity of insulin defined in units is, of course, standard. While not being limited by way of theory, in the present invention, it is believed that the insulin promotes the wound healing by enhancing the transport and utilization of glucose by the cells.

The cellular nutrient medium, used in the present invention, is any nutrient medium having the effect of enhancing the recovery of wounded or atrophic skin tissues when used in combination with the cell growth-stimulating compound. In the preferred embodiment of the present invention, the nutrient media is composed of the components set forth herein, it is mixed with effective amounts of the non-steroidal anabolic hormone or its substitute to form the compositions of the present invention. Preferably, the medium is serum-free.

The cellular media comprises effective amounts of the following constituent: (a) essential; (b) non-essential amino acids; (c) vitamins as previously described; (d) inorganic ions as previously described and (e) glucose; optionally, (f) purines and pyrimidines; (g) other organic compounds; (h) other inorganic ions; (i) trace elements; (j) buffers and indicators and (k) other supplements. Preferably, the cellular nutrient medium used herein contains effective amounts of elements (f) through (k). Serum free nutrient medium is preferred. The preferred serum free nutrient medium is modified MCDB, a well-known medium. Mixtures of standard nutrient media may also be used with favorable results in the instant invention.

While not being limited by way of theory, it is believed that one plausible explanation of the mechanism of accelerated wound healing is that the presence of the anabolic hormone, and in particular, insulin and/or hydroxychalcone (preferably a mixture of at least one of these and most preferably a combination of insulin and MHCP in nutrient medium, further including IGF, selenium, chromium and/or curcuma) in the formulations according to the present invention, promotes the utilization of the nutrient medium and consequentially, growth in situ of the granulation tissue, i.e., within the wound itself. At the same time, the novel formulations may also induce the stimulation of the vascular elements and promote the growth of vascularized granulation tissue preparatory to split skin grafting. The present formulation may in this same way also be useful to promote the healing, growth and regeneration of atrophic skin and to function as atrophic skin adjuvants. The proliferation of vascularized granulation promotes epidermal growth from the peripheral edges of the wound over the vascular substratum and from the deeper layers of the dermis leading to an early closure of the skin over the wound. The mechanism, which might be assumed, is that in the proliferation phase, new capillaries and fibroblasts appear in the wound from the first day on and reach their maximum levels after one week. The new vessels in the granulation tissue originate as budlike structures on nearby vessels, penetrating the wound, become canalized and ramify throughout the wound by cell multiplication.

It is further believed that the function of the nutrient medium is to provide nutrients to the normal, distressed and injured cells and skin that surround or comprise the wound to be treated, in order to enhance the growth and repair mechanisms that are responsible for the healing of the wound. In this way, the nutrient medium functions with the anabolic hormone or the nutrient substitute to promote the normal processes of elaboration, synthesis and growth leading to the healing of the wound and adjacent skin areas. In addition, the gelled media serves to maintain a moist environment surrounding the wound area.

A number of nutrient media, preferably serum free, alone or in combination may be used in the present invention, including commercially available media or other media well known in the art. Examples of such media (all without serum or having had serum removed) include ADC-1, LPM (BOVINE Serum albumin-free), (10 (HAM), F12 (HAM), DCCM1, DCCM2, RPMI 1640, BGJ Medium (Fitton-Jackson Modification), Basal Medium Eagle (BME with the addition of Earl's salt base), Dulbecco's Modified Eagle Medium (DMEM-without serum), Glasgow Modification Eagle Medium (GMEM), Leibovitz L-15 Medium, McCoy's 5 A medium, Medium M199 (M199E—with Eagle's Minimum Essential Medium (MEM-E with Eagle base), Minimum Essential Medium Eagle (MEM-H—with Hank's salt base) and Minimum Essential Medium Eagle) MEM-NAA—with non essential amino acids), among numerous others. These and other useful serum-free nutrient media are available from GIBCO, Grand Island, N.Y., USA and Biological Industries, Bet HaEmek, Israel, among others.

In addition, serum-containing nutrient media may also be used in compositions according to the present invention, but the use of the serum-containing media is less preferred because of the possibility that the serum may be contaminated with microbial agents and because the patient may develop immunological reaction to certain antigenic components contained in the serum.

While a large number of serum free nutrient media may be used in the present invention, a preferred but not the only nutrient media for use in the present invention is modified MCDB 153.

Experiments that were performed to extend the viability of split skin grafts show that the use of modified MCDB 153 medium prolonged the limit of viability from 3 to 9 weeks. Histological examination of specimen indicated a strong attachment of the epidermal layer to the dermal substratum in all specimen kept in the modified MCDB 153 medium at 4°-8°-C.

Hereafter are presented the particular constituents and concentrations of the above groups in MCDB 153.

|  | Concentrations in M |
|---|---|
| Group (a) | |
| Arginine | $1.0 \times 10^{-3}$ |
| Cysteine or Cystine | $2.4 \times 10^{-4}$ |
| Glutamine | $6.0 \times 10^{-3}$ |
| Histadine | $8.0 \times 10^{-5}$ |
| Isoleucine | $1.5 \times 10^{-5}$ |
| Leucine | $5.0 \times 10^{-4}$ |
| Lycine | $1.0 \times 10^{-4}$ |
| Methionine | $3.0 \times 10^{-5}$ |
| Phenylalanine | $3.0 \times 10^{-5}$ |
| Threonine | $1.0 \times 10^{-4}$ |
| Tryptophane | $1.5 \times 10^{-5}$ |
| Tyrosine | $1.5 \times 10^{-5}$ |
| Valine | $3.0 \times 10^{-4}$ |
| Group (b) | |
| Alanine | $1.0 \times 10^{-4}$ |
| Asparagine | $1.0 \times 10^{-4}$ |
| Aspartate | $3.0 \times 10^{-4}$ |
| Glutamate | $1.0 \times 10^{-4}$ |
| Glycine | $1.0 \times 10^{-4}$ |
| Proline | $3.0 \times 10^{-4}$ |
| Serine | $6.0 \times 10^{-4}$ |
| Group (c) | |
| Biotin | $6.0 \times 10^{-8}$ |
| Folate | $1.8 \times 10^{-6}$ |
| Lipoate | $1.0 \times 10^{-6}$ |
| Niacinamide | $3.0 \times 10^{-7}$ |
| Pantothenate | $1.0 \times 10^{-6}$ |
| Pyridoxine | $3.0 \times 10^{-7}$ |
| Riboflavin | $1.0 \times 10^{-7}$ |
| Thiamin | $1.0 \times 10^{-6}$ |
| Vitamin B12 | $3.0 \times 10^{-7}$ |
| Group (d) | |
| Glucose | $6.0 \times 10^{-3}$ |
| Group (e) | |
| Magnesium | $6.0 \times 10^{-4}$ |
| Potassium | $1.5 \times 10^{-3}$ |
| Sodium | $1.5 \times 10^{-1}$ |
| Chloride | $1.3 \times 10^{-1}$ |
| Calcium | 0.1 mmol |
| Group (f) | |
| Adenine | $1.8 \times 10^{-4}$ |
| Thymadine | $3.0 \times 10^{-6}$ |
| Group (g) | |
| Acetate | $3.7 \times 10^{-3}$ |
| Cholin | $1.0 \times 10^{-4}$ |
| i-Inositol | $1.0 \times 10^{-4}$ |
| Putrecine | $1.0 \times 10^{-6}$ |
| Pyruvate | $5.0 \times 10^{-4}$ |
| Group (h) | |
| Phosphate | $2.0 \times 10^{-3}$ |
| Sulphate | $4.5 \times 10^{-6}$ |
| Group (i) | |
| Copper | $1.0 \times 10^{-8}$ |
| Iron | $1.5 \times 10^{-6}$ |
| Zinc | $3.0 \times 10^{-6}$ |
| Group (j) | |
| Bicarbonate | $1.4 \times 10^{-2}$ |
| HEPES | $2.8 \times 10^{-2}$ |
| Group (k) | |
| Ethanolamine | 0.1 mmol. |
| Phosphoethanolamine | 0.1 mmol. |

Weights of each of the above in the medium may be varied within the concentration described herein above to provide formulations workable within the description of the present invention. Preferably, the non-steroidal anabolic hormone to be incorporated into the MCDB 153 composition according to the present invention is a mixture of insulin and/or its substitute at effective concentrations. Most preferably, the anabolic hormone insulin (with or without transferring) or the insulin substitute each included in effective concentrations for promoting wound healing. The effective amount of insulin generally ranges from about 5 ng/ml to about 100 ug/ml and more preferably about 500 ng/ml to about 5 ug/ml within this range. Higher amounts of insulin may be merited where the formulation is stored for longer periods of time.

The synergistic activity of insulin and its nutrient substitute suggests that they will enhance the activity of the indigenous natural occurring insulin in and around the wound whether the wound is traumatic or results from atrophic processes and the concomitant sparse blood supply to the area.

The anabolic hormone insulin was found to impart a maturing stimulus of the growing culture. Insulin may be commercially obtained and generally provided in mU quantities (about 41 ng of insulin). The International Unit of Insulin (SI=System International) is the activity contains in 0.04167 mg (41.67 ug) of the $4^{th}$ International Standard Preparation (1958). The Standard Preparation is quantity of purified Zinc Insulin crystals extracted 52% from Bovine and 48% from Porcine pancreas (se Martindale Pharmacopoeia, $26^{th}$ Ed.).

The formulation according to the present invention may also include an effective amount of an antimicrobial agent, for example, antibiotics, antiviral and antifungal agents, such as griseofulvin and nystatin, and the like. The antimicrobial agent may be added for its ability to treat infections, or alternatively, for its prophylactic effect avoiding an infection. When antimicrobial agents are contemplated for use in the present invention, an amount effective to treat an infection or a prophylactic amount of such agents is chosen. The amount of antimicrobial agent used is that amount typically used in topical application. One of ordinary skill in the art can easily determine the type and amount of antimicrobial agents chosen for use in formulations according to the present invention.

In general the antimicrobial agent may vary widely depending on the efficacy of the agent to be delivered and the prophylactic treatment or the severity of the infection. However, in general, the amount of antimicrobial agent to be used in the present invention will range from about 0.05 ug/ml to about 250 mg/ml with the preferred range of about 50 to about 200 ug/ml. Of course, these ranges will vary depending upon the condition of the infection to be treated as well as the strength of the antimicrobial agent employed. For example, in the case of treatment of fungal infections, the amount of amphotericin used generally ranges from about 0.1 ug/ml to about 100 ug/ml with a preferred concentration of about 0.25 ug/ml. In the case of antibiotics and in particular, penicillin, streptomycin and gentamycin, these agents are generally utilized within the concentration range of about 0.05 ug/ml to about 250 mg/ml with preferred concentration of about 25 ug/ml to about 250 ug/ml.

In the case of the use of antibiotics, any number of antibiotics may be used, including sulfa drugs, penicillin, chloramphenicol and aminoglycosides, among others, but it is preferable to use the broad spectrum antibiotics, for example cephalosporin or tetracycline in a prophylactic amount or alternatively, in an amount effective for treating bacterial infection. In using antibiotics, one of ordinary skill in the art will recognize to minimize or avoid the use of antibiotics that may produce allergic reactions in the treated patients.

In certain embodiments according to the present invention, the formulations as described herein are further formulated with hydrogels or related delivery polymers for delivering the formulation according to the present invention to the wound. In these embodiments, the formulations consists of effective amounts of anabolic hormone insulin or it nutrient substitute with a nutrient media, either alone or in addition to other optional components, are admixed with amounts of a delivery polymer effective for producing a gel, for example a hydrogel polymer derived from HEMA (Hydroxyethylmethacrylate) or NVP (N-vinylpyrrolidone), polyethylene glycol (PEG), polyethylene, gelatin, various carbohydrates, sepharose, agarose, methylcellulose, hydroxymethyl and hydroxyethylcellulose and related hydrophilic cellulose polymers including cellulose, dextran, polyethylene oxide, dextrin-polyethylene, agarose, acrylamide, polyacrilamide, amyloseor collagen to promote wound healing and skin growth. In general, the amount of delivery polymer which is added to the formulations produce a gel generally ranges from about 0.1% by weight to about 20% by weight, preferably about 1% to about 5% or more by weight, depending upon the type of delivery polymer used. The gel compositions according to the present invention preferably contain sufficient water or moisture to maintain the wound environment in a moist state—a condition shown to be beneficial to the wound healing. In addition to accelerating wound healing through the application of the formulations of the present invention, the compositions that are formulated with a delivery polymer also exhibit the added benefit of preventing or slowing the formation of a scab on the wound. While not being limited by way of theory, it is believed that the resultant wound tissue, which remains soft and moist instead of dry and scab-like, produces a beneficial, cosmetically pleasing and increased rate wound healing.

In addition to solution, gel or hydrogels forms, compositions according to the present invention also may be formulated as creams, elixirs, lotions, powders and the like. The various components of the wound treatment compositions according to the present invention may have to be varied in order to maintain effective concentrations for promoting wound healing. When the wound healing compositions are formulated according to the present invention, these compositions may also contain an amount of pharmaceutically acceptable excipient and, in addition, other additive such as diluents, compounding agents, bulking agents, surfactants and the like. One of the ordinary skills in the art will recognize to vary the concentrations of the individual components as a function of the type of delivery vehicle used for the wound treatment compositions in order to facilitate and enhance the wound healing activity of the present formulations.

In a method for treating wounds according to the present invention, the formulations as described hereinabove are topically applied to the wound tissue as a liquid or gel preferably at least once a day and up to six or more times a day. In the case of formulations containing a delivery polymer, preferably as a moisten delivery polymer, the formulations may be administered less frequently then when the formulation are applied as a liquid, for example, once every several days or more. One of ordinary skill in the art will readily be able to determine the amount and frequency of administering the formulation according to the present invention.

The amount of material that is spread on the wound as a treatment will be readily apparent to one of ordinary skill in the art. In general, in solution or in gel form, about 1 cc of the formulation is applied per 1 $cm^2$ of the wound area. Depending upon the depth of the wound to be treated, an amount greater or lesser then the 1 cc of formulation per 1 $cm^2$ of the wound surface may be utilized. In many instances, the depth of the formulation on the wound shall be at least about 2 mm and shall cover the whole surface of the wound.

Materials and Methods of the Present Invention

1. Preparation of Gel-Media

The entire procedure was performed under sterile conditions.

a. Delivery System

One gram of Agarose Type 1-A; Low EEO (Sigma Chemical Co) was dissolved in 10 cc of 2× distilled water. The solution was autoclaved. All preparations of the gel media were made using a final concentration of either 1% Agarose or gelatin.

b. Media

The preferred media contained essential and nonessential amino acids, Vitamins, other organic constituents, major inorganic salts, trace elements and buffers are Supplemented with CaCl, L-glutamine and the non-steroidal anabolic hormone insulin. At concentrations indicated below.

| Component | Concentration in M |
|---|---|
| Amino Acids (L-enantiomers) | |
| Alanine | $1.0 \times 10^{-4}$ |
| Arginine HCl | $1.0 \times 10^{-3}$ |
| Asparagine | $1.0 \times 10^{-4}$ |
| Aspartic Acid | $3.0 \times 10^{-5}$ |
| Cysteine HCl or Cystine | $2.4 \times 10^{-4}$ |
| Glutamic Acid | $1.0 \times 10^{-4}$ |
| Glutamine | $6.1 \times 10^{-3}$ |
| Glycine | $1.0 \times 10^{-4}$ |
| Histadine HCl | $6.0 \times 10^{-5}$ |
| Isoleucine | $1.5 \times 10^{-5}$ |
| Leucine | $5.0 \times 10^{-4}$ |
| Lycine HCl | $1.0 \times 10^{-4}$ |
| Merthionine | $3.0 \times 10^{-5}$ |
| Phenylalanine | $3.0 \times 10^{-5}$ |
| Proline | $3.0 \times 10^{-4}$ |
| Serine | $6.0 \times 10^{-4}$ |
| Threonine | $1.0 \times 10^{-4}$ |
| Tryptophan | $1.5 \times 10^{-5}$ |
| Tyrosine | $1.5 \times 10^{-5}$ |
| Valine | $3.0 \times 10^{-4}$ |
| Vitamins | |
| Biotin | $6.0 \times 10^{-8}$ |
| Folic Acid | $1.8 \times 10^{-6}$ |
| DL-a-lipoic acid | $1.0 \times 10^{-6}$ |
| Niacinamide | $3.0 \times 10^{-7}$ |
| D-panto thenate 1/20a | $1.0 \times 10^{-6}$ |
| Pyridoxine HCl | $3.0 \times 10^{-7}$ |
| Riboflavin | $1.0 \times 10^{-7}$ |

-continued

| Component | Concentration in M |
|---|---|
| Thiamin HCl | $1.0 \times 10^{-6}$ |
| Vitamin B12 | $3.0 \times 10^{-7}$ |
| Other Organic Constituents | |
| Acetate | $3.7 \times 10^{-3}$ |
| Adenine | $1.8 \times 10^{-4}$ |
| Choline chloride | $1.0 \times 10^{-4}$ |
| i-Inositol | $1.0 \times 10^{-4}$ |
| Putrescine 2HCl | $1.0 \times 10^{-6}$ |
| Na Pyruvate | $5.0 \times 10^{-4}$ |
| Thymidine | $3.0 \times 10^{-6}$ |
| Major Organic Salts | |
| $CaCl_2$ | $4.0 \times 10^{-5}$ |
| KCl | $1.5 \times 10^{-3}$ |
| $MgCl_2$ | $6.0 \times 10^{-4}$ |
| NaCl | $1.2 \times 10^{-1}$ |
| $Na_2HPO_3$ | $2.0 \times 10^{-3}$ |
| Trace Elements | |
| $CuSO_4$ | $1.1 \times 10^{-8}$ |
| $FeSO_4$ | $5.0 \times 10^{-6}$ |
| $H_2SeO_3$ | $3.0 \times 10^{-8}$ |
| $MnSO_4$ | $1.0 \times 10^{-9}$ |
| $Na_2SiO_3$ | $5.0 \times 10^{-7}$ |
| $(NH_4)Mo_7)O_2$ | $1.0 \times 10^{-9}$ |
| $NH_4VO_3$ | $5.0 \times 10^{-9}$ |
| $NiCl_2$ | $5.0 \times 10^{-10}$ |
| $SnCl_2$ | $5.0 \times 10^{-10}$ |
| $ZnSO_4$ | |
| Buffers | |
| Hepes | $2.8 \times 10^{-2}$ |
| $NaHCO_3$ | $1.4 \times 10^{-2}$ |
| Non-Steroidal Anabolic Hormone | |
| Insulin | 5 ug/ml |
| Insulin-like MHCP | 0.5 mg/ml |
| Vehicle | |
| Agarose (Sigma A-0169) | 1% |
| EEO (electro endosmosis 0/10-0.15 | |
| Gel Point - 36° C. | |
| Melting Point - 87° C. | |
| Gel Strength - >825 g/cm² for 1% | |
| PH 7-8.5 | | c. Preparation of the Wound Healing Formulation

Ninety cc of the above-defined medium was warmed in a water bath to 40° C. Following autoclaving, 10 cc of the 1% agarose gel solution was allowed to cool to 40° C., and the solution was then added to the medium to produce a homogenous mixture. The mixture was then aspirated into 10 or 20 cc syringes and refrigerated at 4° C.

Preclinical Studies on Animal Model

Hartley-derived albino guinea pigs weighing 300-400 grams were used in this study. The animals were housed in individual cages and fed regularly guinea pig chow and water enriched with vitamin C ad libitum. All Surgical procedures were performed under general anesthesia using Katamin HCl ([d]-2-(o-chlorophenyl)-2-(methylamino)cyclohexanone hydrochloride, available from Park-Davis) 150 mg/kg i.m. All histological sections were prepared using hematoxylene and Eosin stain as well as Mason's trichrome method for collagen.

Each animal was anesthetized and four bilateral symmetrical full thickness skin segments measuring 2×3 cm were excised from the dorsum of each animal, two from the scapular region and two from the lumbar region. After washing the wound with warm saline, the wounds were dressed with the gel at a concentration of about 1 cc/cm², covered with a polyethylene base synthetic membrane Omiderm (Omicron, Israel) and anchored with gauze, elastic adhesive and Retelast netting (Medinet, s.p.a., Italy). The dressing were changed every 48 hours under general anesthesia, at which time the wounds were washed with warm saline to remove any debris and the remaining gel within the wound, measures, photographed and fresh gel was applied and the wounds dressed as described above. At days 4, 6, 8, 10, and 12, the animals were sacrificed and the wounds with the surrounding structures were removed and prepared for histological examination.

The thickness of the newly formed epithelial layer and the underlying granulation tissue were measured using light microscopy (Zeiss) at 100× magnification.

The wound micrographs were analyzed using ImageMeasure (Phoenix Corp., Seattle, Wash.) computerized morphometric program and the experimental results were plotted as graphs showing the fractional change in the area (i.e. the closure rate) of the wounds treated with the gel-media+hormone versus the various controls. The wound closure rate was tabulated and peak closure day (% closure) was determined.

Peak closure rate has been used as the measure of wound healing potency. Peak closure rate is the maximum slope of the Vs, time curve.

$$\frac{Ao - At}{Ao}$$

Peak closure rate indicate the time after the start of the treatment at which tissue healing or growth rate reaches a maximum value (Maximum rate); i.e. when the treatment is optimal.

Figure 1:
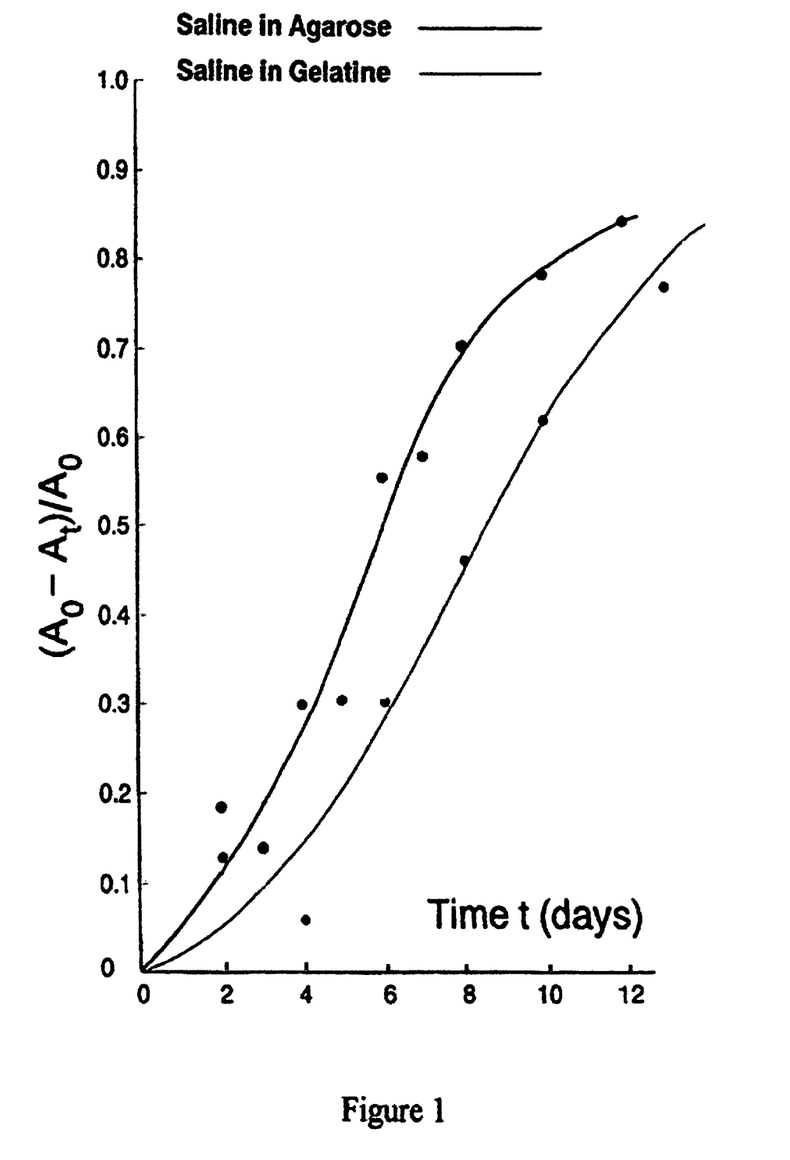

Seven groups of experiments were performed using various combinations of medicaments as controls:

Experiment 1—Gelatin in saline (n=12) vs. Agarose in saline (N12) FIG. 1

Figure 2:
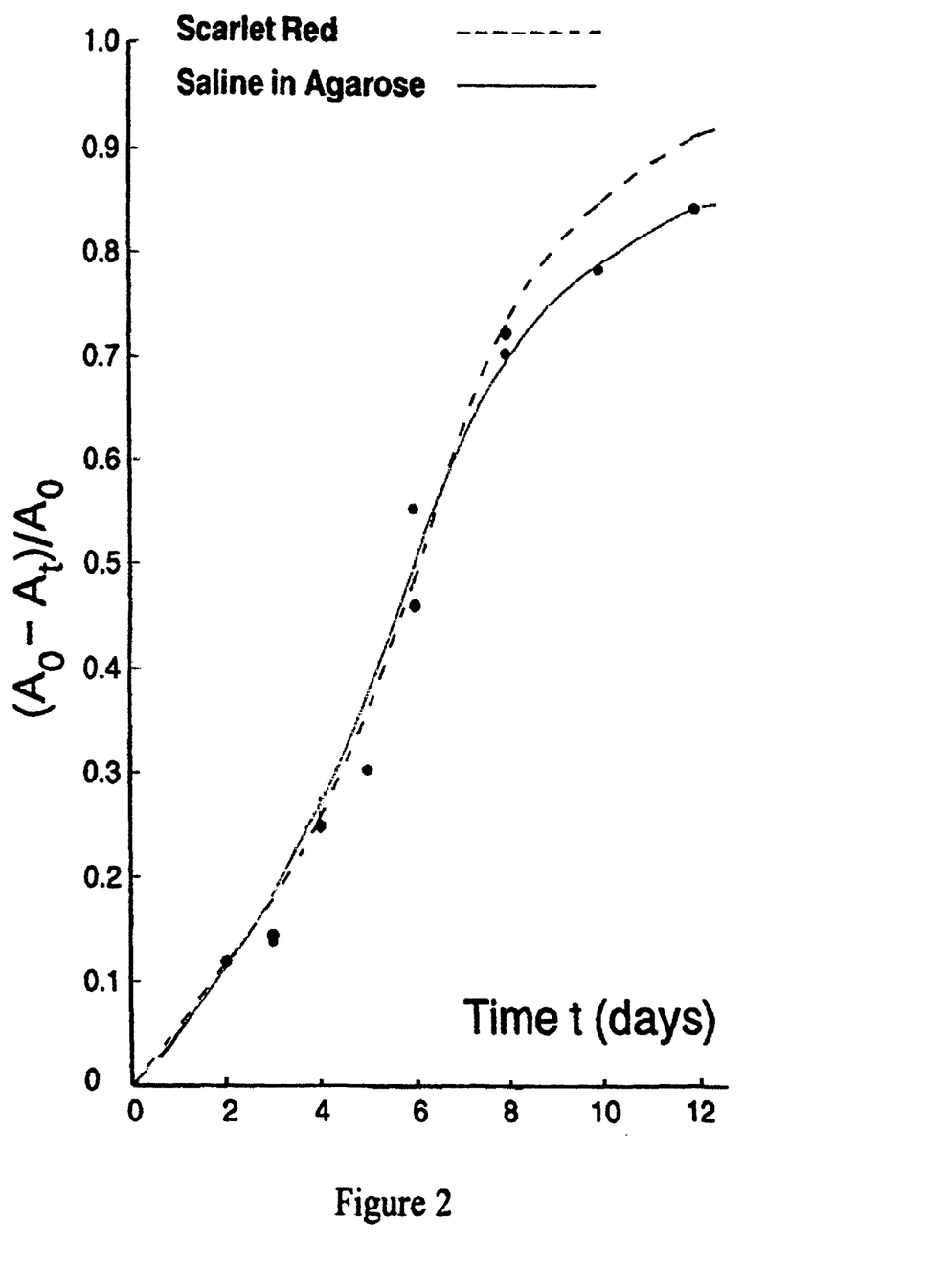

Experiment 2—Test for control—Scarlet red (n=12) and Agarose in saline (n=12) as positive and negative control respectively. FIG. 2

Experiment 3—Agarose in medium supplemented with insulin (n=12) vs. Agarose in medium without insulin (n=12).

Figure 3:
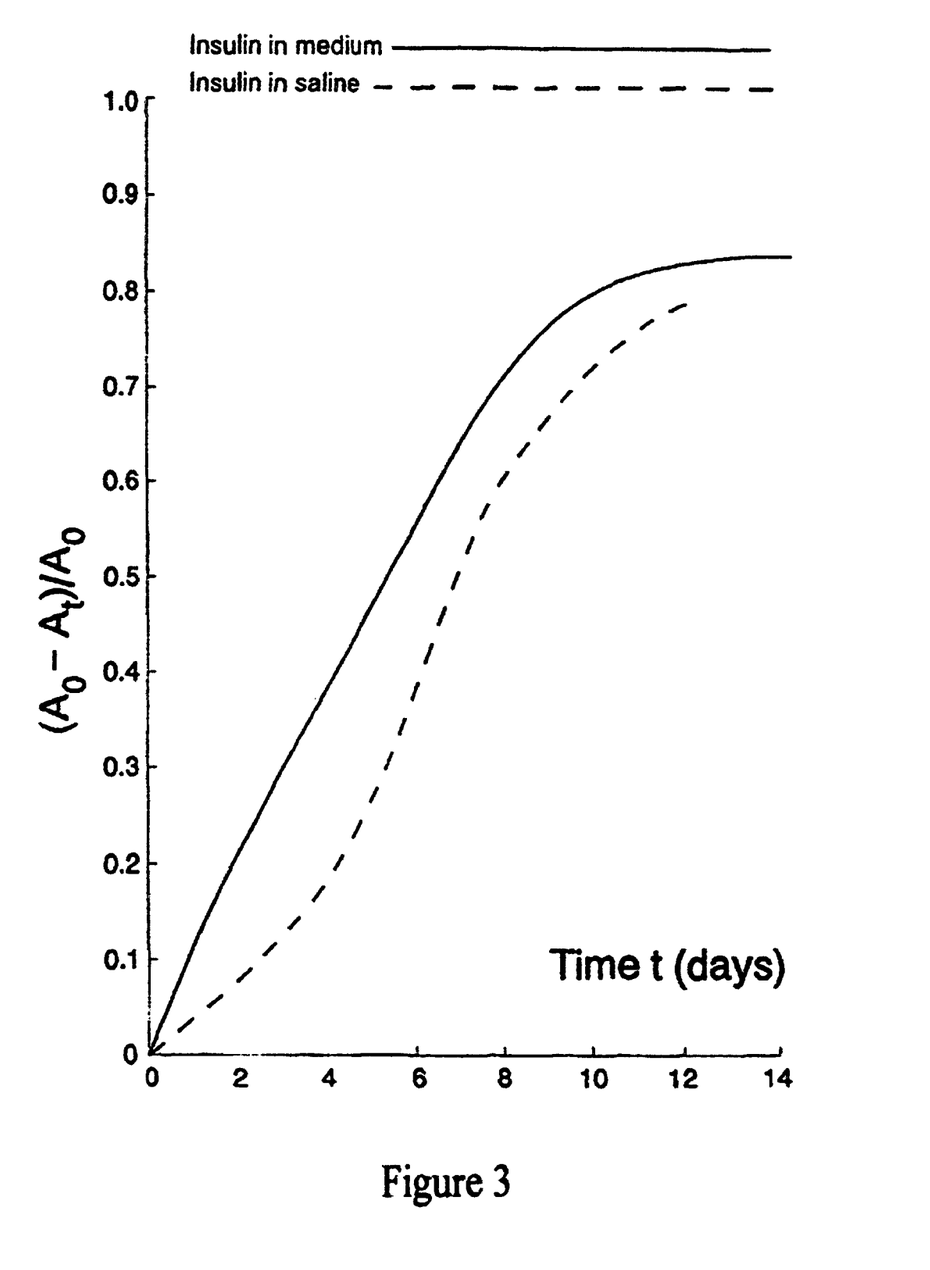

Experiment 4—Agarose in saline with insulin (no medium) (n=33, 5 ug/ml), vs. Agarose in medium containing insulin (n=12) FIG. 3.

Experiment 5—Agarose in saline (n=12) supplemented with insulin vs. Agarose in medium supplemented with insulin (n=12):

Experiment 6—Agarose medium supplemented with insulin without disinfectant compress (n=12) vs. the same medicament plus 10 minutes compress of ESDC (Symbollon Corp.) applied during the change of bandages (n=15).

Experiment 7—Agarose in medium supplemented with insulin (n=12) vs. Agarose in saline supplemented with insulin (n=12).

Test for Formulation Delivery Vehicle

Gelatin and Agarose were prepared in saline and the two gels were used to treat experimental wounds. The rate of closure of the wounds treated with Agarose was faster than the rate of closure of wounds treated with gelatin.

Wound closure comparison indicates that the closure of 50% was 31% faster with Agarose in saline as compared to Gelatin in Saline. Peak closure rate occurred 33% earlier with Agarose in Saline treatment.

Test for Positive and Negative Controls

Scarlet red dressing (O-Tolylazo-oTolylazi-beta-naphthol plus lanolin, olive oil and petroleum from Chesebrough-Ponds, Inc., hospital Products Division, Greenwich, Conn., USA—an azo dye-containing preparation routinely used in hospitals and claimed to increase epithelialization) was used as a positive control and saline in Agarose was used as negative control. The rate of wound closure in each of these formulations was plotted against that of the wounds treated with media+insulin (n=15). Comparison of the wound closure rate indicated that 50% closure was 50% faster with the media+insulin treatment as compared to both controls. Peak closure rate occurred 50% and 40% later for saline and scarlet red treatment respectively, as compared to media+insulin.

Treatment with Media+Insulin in Agarose Vs. Media in. Agarose Alone

Treatment with media+insulin formulation induced accelerated wound healing compared to treatment with media prepared in Agarose without insulin. The rate of wound closure using the media alone was similar to that of the wound treated with saline in Agarose.

Since the media alone did not induce any stimulatory effect on the wounds closure, the presence of insulin appeared essential for utilization of the media by the cells. Comparison of wound closure rate indicates that closure of 50% was 60% slower with media alone compared to media+insulin. Peak closure rate occurred 50% earlier in media+insulin treated wounds compared to wound treated with media alone.

Test of Agarose in Media+Insulin with and without ESDC Disinfectant Compress

The rate of wound closure with the media+disinfectant treatment was initially faster than that of the wounds treated with media alone. However, on the $2^{nd}$ day the rate of the wound closure for wounds treated with media+insulin accelerated and was faster than the closure rate of wounds treated with the addition of the disinfectant compress. After the initial period of time, the disinfectant exerted cumulative cytotoxic effect that slows the healing process.

Comparison of wound closure rate indicated that the closure of 50% was 45% slower with the disinfectant treatment.

Peak closure rate occurred 100% later with the disinfectant treatment compared to medium+insulin without the disinfectant treatment.

Comparison of Wound Closure Rate

| Closure % (day) | 50% | Peak Closure Day (% Closure) |
|---|---|---|
| Media + insulin | 3.5 | 3.0 (30%) |
| Saline in Agarose | 6.0 | 6.0 (50%) |
| Saline in Gelatin | 8.5 | 9.0 (50%) |
| Scarlet Red | 6.0 | 5.0 (35%) |
| Media + Disinfectant | 5.0 | 6.0 (50%) |
| Insulin | 5.0 | 3.0 (30%) |
| Media alone | 7.0 | 6.0 (40%) |
| Saline + Insulin | 7.0 | 7.0 (50%) |

Conclusions

The following conclusions can be drawn from the results of the experiments presented herein.

Drug Delivery System

Using the formulations employed, use of Agarose improves wound closure rate as compared to Gelatin. In particular, closure of wound treated with gelatin in saline is about 33% slower than the closure of wounds treated with Agarose in saline.

Controls—Scarlet Red and Saline

The use of Scarlet red dressing as a positive control and Saline as a negative control yielded similar results and slower closure when compared with media+Insulin treatment.

The presence of insulin in the presence of medium produces significant wound healing benefit (wound closure is significantly higher). Treatment with Gel media (Agarose) without insulin was slower than media with insulin and similar to the rate of closure of Agarose in saline.

The presence of insulin in media evidenced significantly wound-healing activity vs. insulin in saline.

The use of Agarose in media containing insulin produced a scar that had a soft tissue texture and a smooth surface (an unexpected result). It produced a more aesthetic and natural looking surface compared to scarlet red or saline. In most instances, neither bulging nor any indentation occurred and the level of the scar tissue is continuous with the conformation of the surrounding non-wounded skin. The texture of the scar is also similar to that of the surrounding non-wounded tissue and discoloration eventually dissolved.

The focus of our interest primarily was the wound closure and our results using the animal model point to the efficacy of media supplemented with insulin formulation according to the present invention, regardless whether the rate of the wound closure was due to wound contraction or epithelialization or to combination of the two. With these mechanisms taken into account, the exponential decrease in wound area was nevertheless, significantly faster using media supplemented with insulin. The various controls used in this study illustrate that, both media alone and insulin alone, individually or together did not achieve the closure rates for wounds treated with both. Furthermore, negative (scarlet red) and positive (Saline) controls yielded similar and slower rates of closure.

Since trace quantities of growth factors and constitute part of the wound exudates (Freshney et. al.), none were added to the formulation of the gel media. While not being limited byway of theory, it is our hypothesis that the application of the gel media into the wound space created a complex, biologically active substrate which may act with the autologous growth factors which, in turn, reinforce the biological activity of the gel. The gel media combined with properties and characteristics of a biologically active material that, in addition, contains all the nutritional requirements, for cellular proliferation. Our results regarding the gel's efficacy appear to agree with earlier findings of Mulder, G. D et. al. who claimed that early wound exudates induced cellular proliferation. The animal model presented herein imposes certain limitations: wounds are clean, surgically made and uncomplicated by contamination. This point is important since the gel media provides a growth substrate for bacteria. It is believed that, in contaminated wounds, a bacteriogram followed by or concomitant with specific antibiotics or disinfectant treatment in combination with the gel media treatment may be indicated.

This invention has been described in terms of specific embodiments set forth in detail herein, but it should be understood that these are by way of illustration and the invention is not necessarily limited hereto. Modifications and variations will be apparent from the disclosure and may be resorted to without departing from the spirit of the invention s those skilled in the art will readily understand. Accordingly, such variations and modifications are considered to be within the purview and scope of the invention and the following claims.

Clinical Studies

Among the common treatments for chronic atrophic wounds, moist dressing is used to create optimal environment and to prevent desiccation of the wound bed. Enriched cell culture medium supplemented with insulin was gelled in 1% agarose. The gel was applied to the surface of the wound (1 ml/cm$^2$) once a day. All wound included in the study were clinically clear of infection, following topical antiseptics or antibiotics. Etiology of the wounds was varied from venous and/or arterial insufficiency to insulin-dependant and non-dependant diabetic ulcers, or combinations of the above.

A total of 288 wounds were within the inclusion criteria, with only contaminated and neoplastic wounds excluded. About 80% of the patients were ambulatory and the wound were examined by the attending physician every 7 to 14 days at an outpatient clinic. The remaining 20% were admitted to the study while hospitalized.

Healing started 7-14 days after the initial treatment. The criterion for success was determined on complete wound closure that was attained in 189 of the 288 patients (65.6%). The average time required for healing of the wounds caused by systemic pathologies (n=181) and those based on regional status (n=107) were 12 and 4.4 weeks respectively, compared with 290 and 10.3 weeks of previous conventional treatment. In 19 extensive wounds, when vascularization and granulation tissue growth started, a successful surgical closure was attained.

Most of he wounds in patients that did not continue the treatment (34.4%) exhibited reduction of wound volume ranging from 11% to 98% of the initial volume. The reasons for discontinued treatment ranged from difficulties in reaching the clinic for the weekly examination rather then reasons directly related to the treatment itself and occurred in the early stages of the treatment. Thus the healing was rapid with minimum scaring and pain. No side effects or allergic reactions were reported or observed.

Case 1

An 80-year-old male was a non-insulin-dependant patient. He suffered from venous insufficiency, asthma controlled by prednisone, and from siderblastic anemia. He presented with a two years old leg ulcer which previously was treated with antiseptics. The treatment with the gel lasted 4 months partially in the hospital and later on an ambulatory basis.

Case 2

A 69-years-old male patient who had a history of 45 years old traumatic injury resulting in lymphostasis and lymphoededema of both lower extremities was admitted into the study. He had multiple leg ulcers which were continuously treated over the years with every conceivable medication or technique. The ambulatory treatment with the gel lasted 4 months for one of the ulcers and five months for complete closure of all he ulcers.

Case 3

A 73-years-old male with venous insufficiency of both legs presented an off/on leg ulcer of 19 years duration. Previous treatments included antiseptics and topical antibiotics; Granuflex was used for at least 2 months. Ambulatory treatment with the gel lasted 3 months after which complete closure was obtained.

Failure of healing is attributed, among other factors, to deficiency of important minerals, vitamins and other nutrients in the wound fluid. Since the chronic wound, ischemic conditions prevail, healing is hindered by the lack of those blood borne nutrients. The gel treatment aims to change microenvironment of the chronic atrophic wound thereby affecting the metabolic processes in the wound cells.

It has been shown that the physiochemical composition of the wound fluid is quantitatively similar but not identical to serum. Shelling et. al. reported that the main difference is in the salt concentration; in the wound fluid potassium and calcium are higher and sodium and phosphate are lower. Furthermore, White et. al. claim that there is less protein, glycoproteins, lipids and globulins. These differences decrease as the wound heals and cellular metabolic requirements return to normal.

REFERENCES

Linge C. Use of insulin containing composition for wound treatment. 2010 January-February 18(1):80-8 Epub 2009

Alt S. Kuroki Tosh A., Methods and pharmaceuticals compositions for healing wounds. Mol. Biol. 2001 November: 21(22):7852-7861.

Barrio L. F, Polansky M. M, Anderson R. A, Cinnamon and brewer's yeast as influenced by albumin. Horm Metab Res. 2004 February: 36(2):119-25

Karlee J. T. Stapelton S. R. Cinnamon extract boosts insulin. Cell Molecular Science 2000 December; 57(13-14):1874-9, 2000

Karalee J. T., Anderson R. A., Graves. D. J. Hydroxychalcone derived from cinnamon functions as mimetic for insulin in 3T3-L1adipocytes. Journal of the American College of Nutrition. Vol. 20 Number (4), 327-336, 2002

Lindenbaum E. S., Tendler M., Beach D. Serum-free cell culture medium induces acceleration of wound healing in Guinea Pigs. Burns Vol. 21, No 2, pp. 110-115, 1995

Lindenbaum E. S., Har-Shai, Ullmann Y. et al., Preliminary clinical trials of serum-free cell culture medium as a treatment for chronic atrophic wounds. Euro. J. Plastic Surgery 20; 115-121, 1997.

Lindenbaum E. S. et al. Stimulated healing of recalcitrant wounds by topical application of enriched cell culture medium: A Clinical Report. Plastic and Reconstructive Surgery, Vol. 108, number 1 p 104-113, 2001

Freshney, R. J., Culture of animal cells. R. Liss, Inc., N.Y., 1988, 2$^{nd}$ edition, pp 239-241 and Hayward and Robinson, Animal models of wound contraction In: *Clinical and Experimental Approaches to Dermal and epidermal Repair; Normal and Clinical Wounds*, pp 301-312, Wiley-Liss, Inc. 1991.

Mulder, G. D, if wounds could talk. *Clinical and Experimental Approaches to Dermal and epidermal Repair; Normal and Clinical Wounds*, pp 55-66, 1991, Wiley-Liss, Inc.

Shelling J A, Joel W. Shurley H W Fractional analysis of the experimental wound fluid. Proc Soc Exp Biol. Med 89:189-192. 1955.

White B N, Shelter M R, Shurley M et. al. Wound healing investigation of protein, glycoprotein and lipids of experimental wound fluid in the dog. Proc Soc Exp Biol. Med 101:353-356. 1959.

Kamath J. V., Rana A. C., and Cowdhury A. R., Pro-healing effect of *Cinnamomum zeylanicum* bark. Phytother Res.: 17(8):970-2 September 2003.

Andeson R. A., Broadhuirst C. L., Polansky M. M., Schmit W. F., Khan A., Flanagan V. P., Schoen N. W., Graves D. J., Isolation and characterization of polyphenol type-A polymers form cinnamon with insulin-like biological activity. J. Am Coll Nutr.: 20(4):327-36. August 2001.

Majno G. The Healing Hand. Commonwealth fund publication September 1991

Nakao H., Yamazaki M., Tsuboi R., Ogawa H., Mixture of sugar and povidone-iodine stimulates wound healing by activating keratinocytes and fibroblast function. Arch Dermatol Res. (4); 175-82 September 2006

The invention claimed is:

1. A wound healing composition consisting of:
   an effective amount of insulin of about 5 ng/ml to about 100 µg/ml or methyl hydroxy chalcone polymer (MHCP) of about 0.01 mg/ml to about 1 mg/ml;
   at least one component selected from the group of insulin-like growth factor (IGF), polyphenol type-A polymer, chromium; curcuma and mixtures thereof in combination; and
   a cellular nutrient medium, wherein the cellular nutrient medium is serum-free.

2. A delivery system consisting of the composition of claim 1 and a delivery polymer.

3. A method for treating a skin wound with a wound healing composition comprises the steps of:
   formulating the wound healing composition consisting of:
      an effective amount of insulin of about 5 ng/ml to about 100 µg/ml or methyl hydroxy chalcone polymer (MHCP) of about 0.01 mg/ml to about 1 mg/ml; at least one component selected from the group of insulin-like growth factor (IGF), polyphenol type-A polymer; chromium; curcuma and mixtures thereof in combination; and a cellular nutrient medium, wherein the cellular nutrient medium is serum-free; and
   topically applying the formulated wound healing composition to the skin wound.

4. A method of formulating a wound healing composition comprises formulating a delivery system consisting of the composition of claim 3 and a delivery polymer.

* * * * *